(12) United States Patent
Beck

(10) Patent No.: US 11,039,678 B2
(45) Date of Patent: Jun. 22, 2021

(54) FIRST RESPONDER DUTY BELT ON AIR

(71) Applicant: Kevin Thomas Beck, Arroyo Grande, CA (US)

(72) Inventor: Kevin Thomas Beck, Arroyo Grande, CA (US)

( * ) Notice: Subject to any disclaimer, the term of this patent is extended or adjusted under 35 U.S.C. 154(b) by 89 days.

(21) Appl. No.: 16/517,614

(22) Filed: Jul. 21, 2019

(65) Prior Publication Data

US 2020/0022485 A1 Jan. 23, 2020

Related U.S. Application Data

(60) Provisional application No. 62/701,724, filed on Jul. 21, 2018.

(51) Int. Cl.

| | |
|---|---|
| *A45F 3/14* | (2006.01) |
| *A41F 9/02* | (2006.01) |
| *A61F 5/32* | (2006.01) |
| *A61F 5/34* | (2006.01) |

(52) U.S. Cl.
CPC ............. *A45F 3/14* (2013.01); *A41F 9/02* (2013.01); *A61F 5/32* (2013.01); *A61F 5/34* (2013.01); *A45F 2003/144* (2013.01)

(58) Field of Classification Search
CPC ........ A45F 3/14; A45F 2003/144; A41F 9/02; A61F 5/32; A61F 5/34
USPC ...................................................... 224/660
See application file for complete search history.

(56) References Cited

U.S. PATENT DOCUMENTS

| 4,135,503 | A | * | 1/1979 | Romano | A61F 5/028 128/118.1 |
| 4,552,135 | A | * | 11/1985 | Racz | A61F 5/028 128/DIG. 20 |
| 4,682,587 | A | * | 7/1987 | Curlee | A61F 5/028 128/DIG. 20 |
| 4,756,306 | A | * | 7/1988 | Curlee | A61F 5/028 602/19 |
| 4,991,573 | A | * | 2/1991 | Miller | A61F 5/028 128/106.1 |
| 5,062,414 | A | * | 11/1991 | Grim | A61F 7/007 602/19 |
| 5,195,948 | A | * | 3/1993 | Hill | A61F 5/028 602/19 |
| 5,205,814 | A | * | 4/1993 | Lundrigan | A61F 5/028 128/DIG. 20 |
| 5,316,022 | A | * | 5/1994 | Schiek, Sr. | A61F 5/028 128/876 |

(Continued)

*Primary Examiner* — Nathan J Newhouse
*Assistant Examiner* — Lester L Vanterpool

(57) ABSTRACT

A system provides an under belt that includes: a first under belt side including a first hook and loop fastener strip, a second under belt side connected to the first under belt side where the second under belt side includes a first heavy duty material outer portion. The under belt further includes an inner under belt portion disposed between the first under belt side and the second under belt side. The inner under belt portion including padding material. A middle belt includes multiple expandable padding portions. A duty belt includes: a center duty belt portion having a first duty belt side and a second duty belt side, a first elastic end attached to the center duty belt portion and a first belt buckle portion, and a second elastic end attached to the center duty belt portion and a second belt buckle portion.

20 Claims, 15 Drawing Sheets

(56) References Cited

U.S. PATENT DOCUMENTS

| | | | | |
|---|---|---|---|---|
| 5,388,274 A * | 2/1995 | Glover | .................... | A61F 5/028 128/100.1 |
| 5,450,858 A * | 9/1995 | Zablotsky | ............... | A61F 5/012 128/876 |
| 5,464,136 A * | 11/1995 | Eddy | ....................... | A45F 5/021 224/666 |
| 5,470,000 A * | 11/1995 | Munoz | ..................... | A45F 5/02 2/300 |
| 5,586,969 A * | 12/1996 | Yewer, Jr. | ............... | A61F 5/028 128/101.1 |
| 5,628,721 A * | 5/1997 | Arnold | .................... | A61F 5/028 128/118.1 |
| 5,693,006 A * | 12/1997 | Slautterback | ........... | A61F 5/028 602/19 |
| 6,053,883 A * | 4/2000 | Schiek, Sr. | ............. | A61F 5/028 602/19 |
| 6,755,799 B2 * | 6/2004 | Toda | ....................... | A61F 5/028 2/311 |
| 7,001,350 B2 * | 2/2006 | Grosso | .................... | A61F 5/028 128/876 |
| 7,364,558 B2 * | 4/2008 | Weaver, II | .............. | A61F 5/028 297/230.1 |
| 7,575,136 B2 * | 8/2009 | Kernkamp | ................ | A45F 3/14 224/158 |
| 7,900,278 B2 * | 3/2011 | Pittman | ................. | F41C 33/046 2/310 |
| 8,591,445 B2 * | 11/2013 | Serola | .................... | A61F 5/028 602/19 |
| 9,339,102 B2 * | 5/2016 | Iosilevich | ................. | A45F 3/14 |
| 9,504,595 B2 * | 11/2016 | Josefek | ................... | A61F 5/028 |
| 2006/0206992 A1 * | 9/2006 | Godshaw | ................ | A61F 5/028 2/338 |
| 2016/0227861 A1 * | 8/2016 | May | ........................ | A45F 5/021 |

* cited by examiner

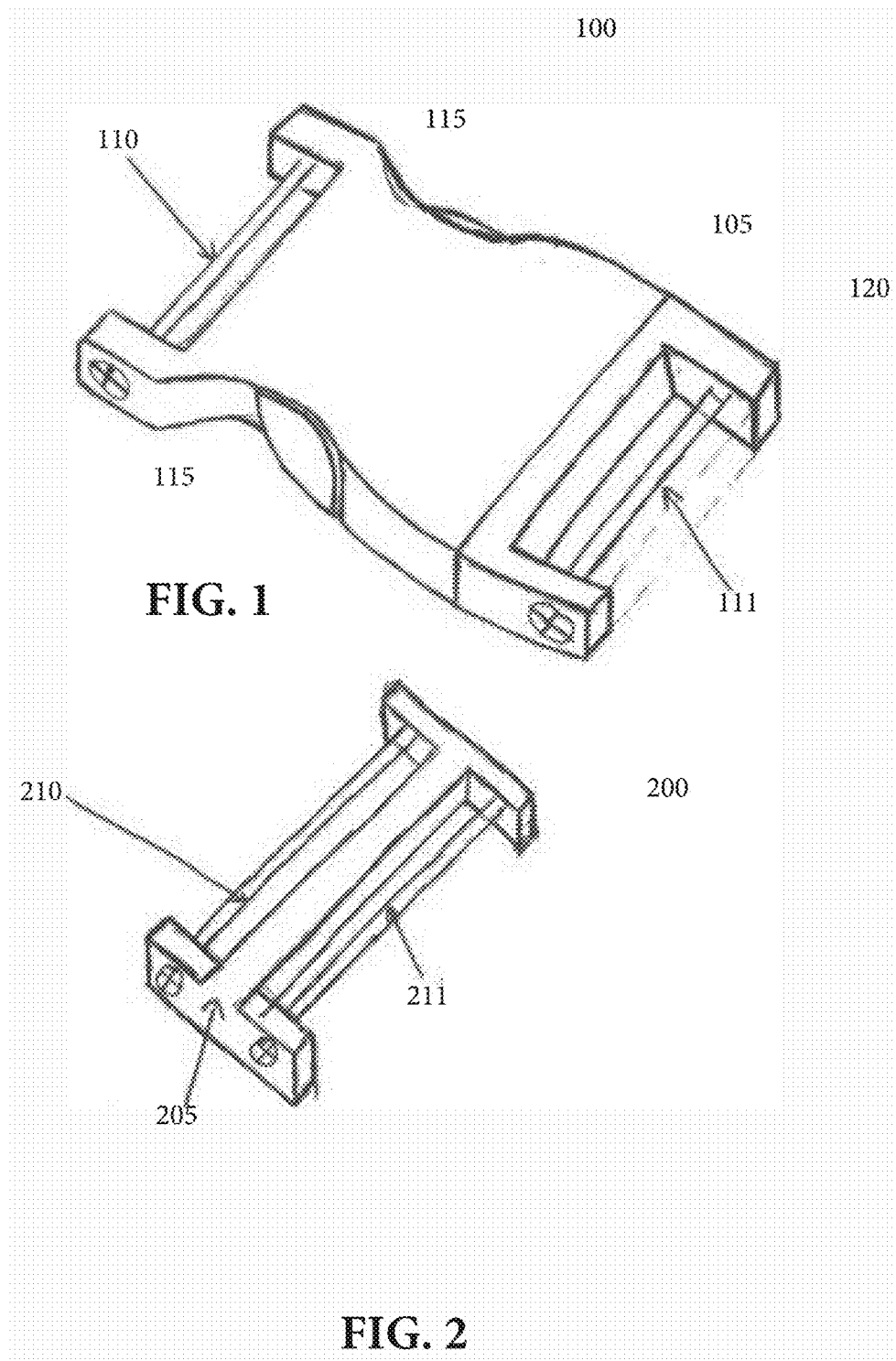

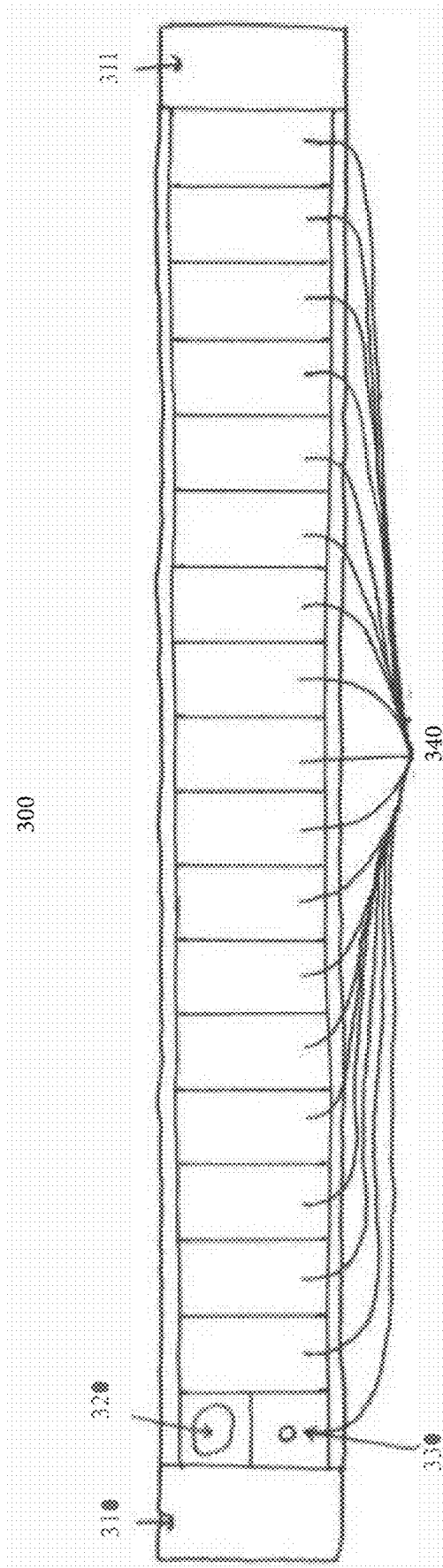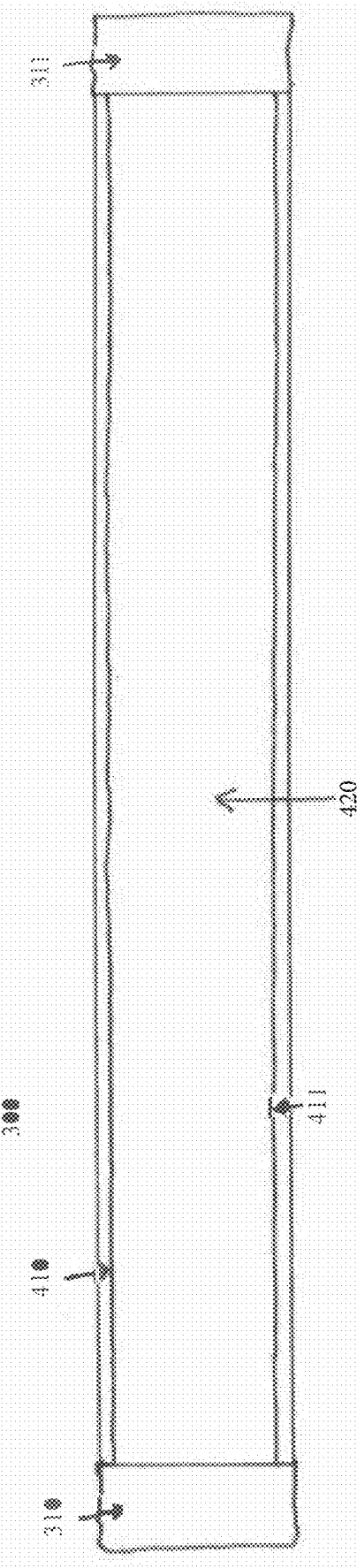

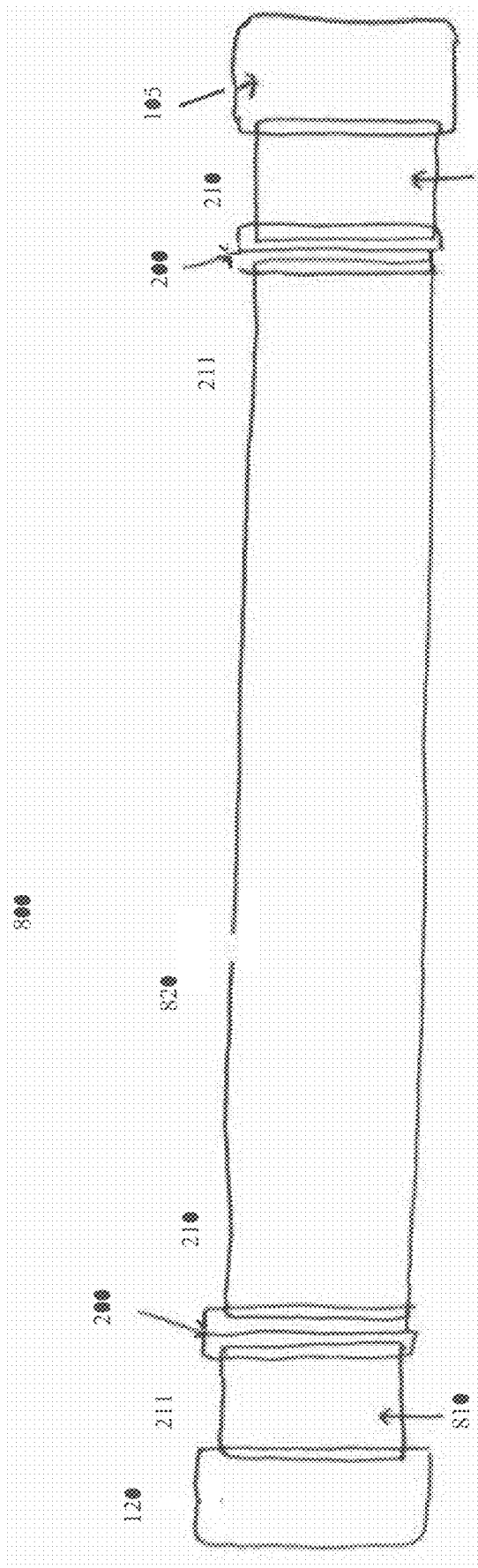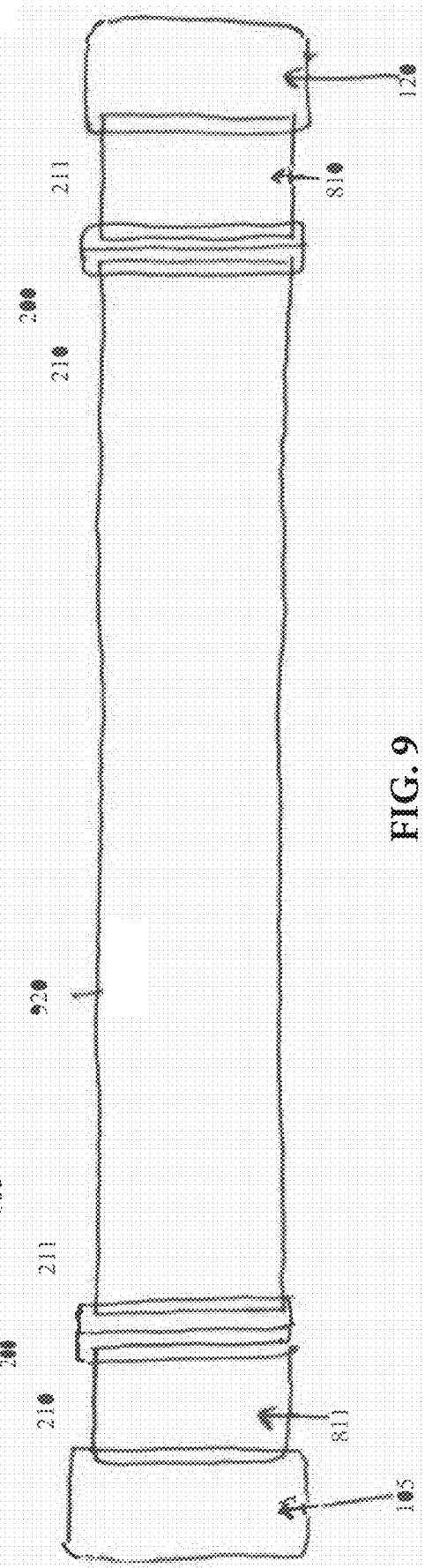
FIG. 8
FIG. 9

FIRST RESPONDER DUTY BELT ON AIR

CROSS-REFERENCE TO RELATED APPLICATIONS

This application claims the priority benefit of U.S. Provisional Patent Application Ser. No. 62/701,724, filed Jul. 21, 2018, which is incorporated herein by reference in its entirety.

BACKGROUND

Back issues and sciatica pain are common ailments for first responders. A first responder is someone who is designated or trained to respond to an emergency. This can include police officers, military and medics. Almost all of first responders are required to wear a duty belt with their uniform. Duty belts must be worn at all times since they are considered a part of the first responders' uniform. The duty belt holds equipment for the first responder to perform their daily duties. This type of equipment may include: flashlight, handcuffs, taser, baton, pepper spray, a firearm, extra ammunition magazines and other tools essential to the job. The weight of a duty belt can reach up to 20 pounds. First responder duty belts can press against their lower back and cause discomfort to the sciatic nerve causing sciatica.

SUMMARY

One or more embodiments relate to first responder duty belts with adjustable padding. One embodiment includes an under belt that includes: a first under belt side including a first hook and loop fastener strip, a second under belt side connected to the first under belt side where the second under belt side includes a first heavy duty material outer portion. The under belt further includes an inner under belt portion disposed between the first under belt side and the second under belt side. The inner under belt portion including padding material. A middle belt includes multiple expandable padding portions. A duty belt includes: a center duty belt portion having a first duty belt side and a second duty belt side, a first elastic end attached to the center duty belt portion and a first belt buckle portion, and a second elastic end attached to the center duty belt portion and a second belt buckle portion.

These and other features, aspects and advantages of the embodiments will become understood with reference to the following description, appended claims and accompanying figures.

BRIEF DESCRIPTION OF THE DRAWINGS

For a fuller understanding of the nature and advantages of the embodiments, as well as a preferred mode of use, reference should be made to the following detailed description read in conjunction with the accompanying drawings, in which:

FIG. 1 illustrates a heavy duty belt buckle, according to one embodiment;

FIG. 2 illustrates a heavy duty tri-glide, according to one embodiment;

FIG. 3 illustrates an internal view of an under belt with an inflatable air chamber system, according to one embodiment;

FIG. 4 illustrates a front view of the under belt with the inflatable air chamber system, according to one embodiment;

FIG. 8 illustrates a rear view of a duty belt, according to one embodiment;

FIG. 9 illustrates a front view of the duty belt, according to one embodiment;

DETAILED DESCRIPTION

Figure 5:
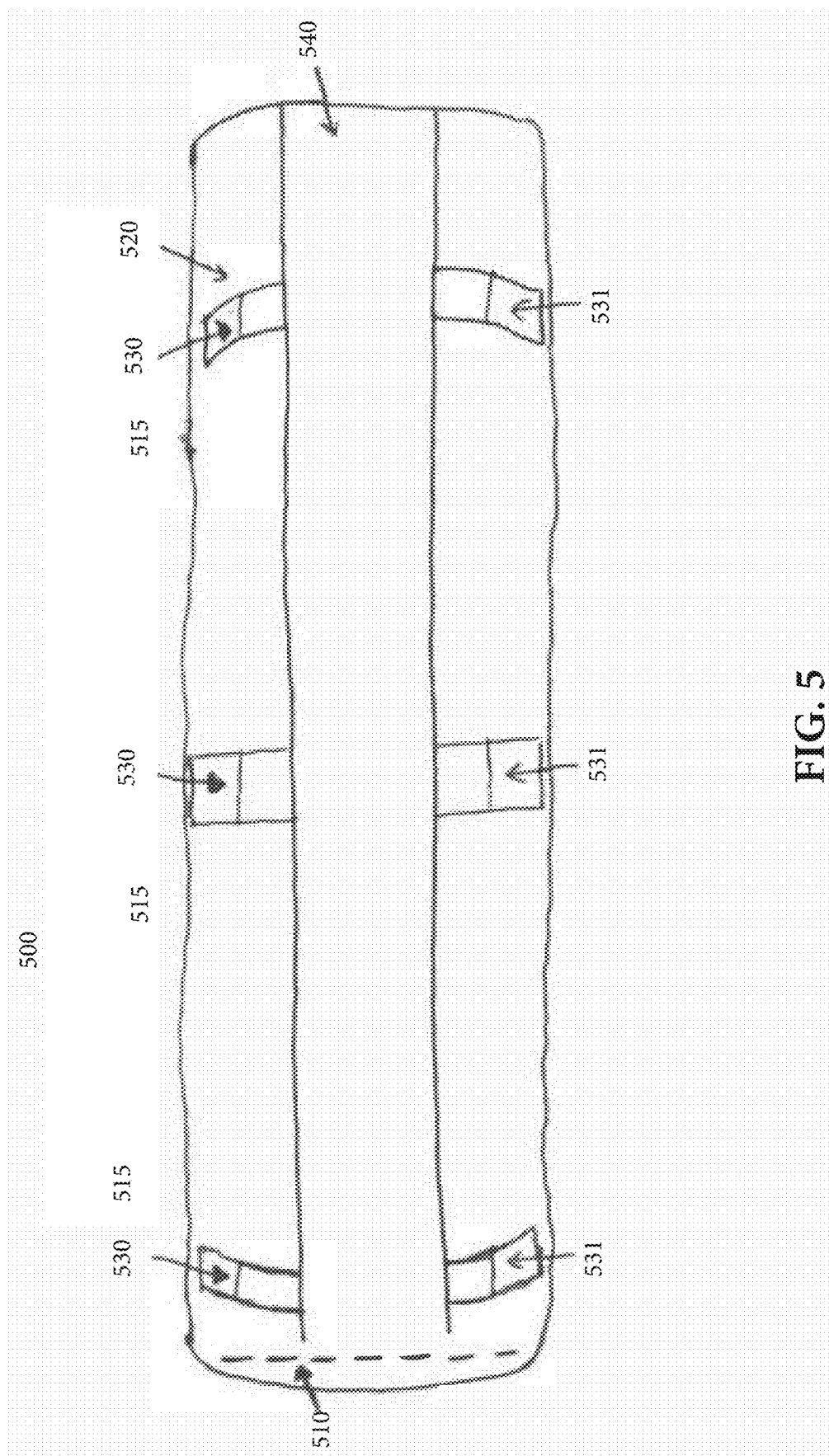
FIG. 5 illustrates a rear view of a duty belt system inflatable pad, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

One or more embodiments provide a duty belt system with adjustable air padding. One embodiment provides a manually adjustable air chambered padding that is disposed between a user's lower back and the equipment on a user's duty belt, which is mandatory to perform their work for their occupation. In one embodiment, the duty belt system includes a pant belt (e.g., 1½ inch wide, etc.) with adjustable air chambers (e.g., vertical chambers, a belt pad (e.g., 5 inches wide, etc.) with adjustable air chambers (e.g., vertical air chambers), a fully adjustable duty belt (e.g., 2¼ inches wide, etc.) and a heavy-duty belt buckle (e.g., a heavy duty plastic, etc. side release buckle; e.g., 2¼ inches wide, etc.). The belt system provides air chambered padding to users when they are in a seated position, preventing their equipment from pressing against their lower back/hips. The belt system evenly distributes the weight of the equipment attached to their duty belt around the user's back eliminating belt pinch and preventing injury to the sciatic nerve. The duty belt system's adjustable design provides for the user to not having to constantly adjust their belt when wearing changing to different uniforms.

One embodiment includes a system that provides an under belt that includes: a first under belt side including a first hook and loop fastener strip, a second under belt side connected to the first under belt side where the second under belt side includes a first heavy duty material outer portion. The under belt further includes an inner under belt portion disposed between the first under belt side and the second under belt side. The inner under belt portion including multiple first expandable chambers. The system further includes a duty belt having: a center duty belt portion having a first duty belt side and a second duty belt side, a first elastic end removably attached to the center duty belt portion and a first belt buckle portion, and a second elastic end removably attached to the center duty belt portion and a second belt buckle portion. The first duty belt side includes a second hook and loop fastener strip. The second duty belt side includes a second heavy duty material outer portion. The under belt is removably attached to the duty belt.

One or more embodiments provide the wearer optimal pressure relief, adjustable firmness and a light weight stable duty belt platform. One or more embodiments reduce the probability of incurring lower back pain in duty belt users, which will ultimately lower the amount of workers compensation cases, medical time off, insurance costs, etc.

FIG. 1. illustrates a heavy duty belt buckle 100, according to one embodiment. In one embodiment, the belt buckle 100 includes a first portion 105 and a second portion 120, which is inserted into the first portion 105. The second portion 120 includes flexible locking portions 115 that flex outwards and lock within openings of the first portion 105. To release the second portion 120 from the first portion 105, the flexible locking portions 115 are pressed inwards, which releases the flexible locking portions 115 from the first portion 105. In one embodiment, the belt buckle 100 includes a first removable pin 110 and a second removable pin 111. In some embodiments, the first removable pin 110 and the second removable pin 111 are made of stainless-steel. In other embodiments, the first removable pin and the second removable pin are made of other metals or metal alloys that are sealed or otherwise rust-free materials.

In one example embodiment, the belt buckle 100 is 2¼ inch in width. In other example embodiments, the belt buckle 100 may be sized according to pant belt loops, e.g., between 2 inches and 3 inches. In one embodiment, the belt buckle 100 is made of heavy duty hardened plastic. In some embodiments, the belt buckle 100 may be include components made of other heavy duty materials, such as metals, metal alloys, etc.

FIG. 2. illustrates a heavy duty tri-glide buckle 200, according to one embodiment. i-gild (also known as triglide slides or plastic slides) are plastic-side buckle-strap adjusters that are ideal for lightweight applications and outdoor uses. Used in conjunction with the belt buckle 100, the triglide 200 allows for a fairly large range range of sizes in collars, and a number of other accessories. In one embodiment, the tri-glide 200 includes a first removable pin 210 and a second removable pin 211 connected to the body 205. In one example embodiment, the first removable pin 210 and the second removable pin 211 are made of stainless steel. In some embodiments, the first removable pin 210 and the second removable pin 211 are made of other metals or metal alloys that are sealed or otherwise rust-free materials.

In one example embodiment, the tri-glide 200 is 2¼ inch in width. In other example embodiments, the tri-glide 200 may be sized according to pant belt loops, e.g., between 2 inches and 3 inches. In one embodiment, the tri-glide 200 is made of heavy duty hardened plastic. In some embodiments, the tri-glide 200 may be include components made of other heavy duty materials, such as metals, metal alloys, etc.

FIG. 3. illustrates an internal view of an under belt 300 with an inflatable air chamber system, according to one embodiment. In one embodiment, the under belt 300 has a width of 1½ inches and includes inflatable air chambers 340 and hook and loop fastener (e.g., heavy duty hook and loop fastener material) belt buckles (or connectors/couplers) 310 and 311 on opposite ends. In other embodiments, the under belt 300 may be sized as desired, such as between 1 inch in width to 3 inches in width, and may have multiple lengths, such as between 28 inches or less to 50 inches or greater (i.e., sized as traditional belts). In some embodiments, the under belt 300 is constructed with a heavy-duty nylon material (or other similar material) on one exterior side (inner side) and a heavy-duty hook and loop material 420 (FIG. 4) on the other exterior side (outer side).

In some embodiments, the multiple vertical (e.g., rectangular, oval, polygonal, etc.) air chambers 340 are made with a heavy-duty rubber material are disposed between (within) each of the exterior sides of the under belt 300. In some embodiments, a manual air pump system is attached, which will allow the wearer to adjust the firmness of the belt. In one example embodiment, an air pump pad 320 allows pumping of air into the air chambers 340. In one embodiment, each air chamber 340 includes a separate air tube to allow for inflation/deflation of the respective air chamber 340. In other embodiments, the air chambers 340 are connected to one another in groups or all-together. In one embodiment, a pressure release valve 330 provides for deflation of air from the air chambers 340.

In one embodiment, the air pump pad 320 is connected to a manual air pump and activated by pressing the air pump pad 320 multiple times until a desired amount of air is pumped into the air chambers 340. In other embodiments, the air pump pad 320 is a switch connected to a battery powered electric air pump, or a valve connected to a compressed air system (e.g., a small compressed air cylinder that releases the compressed air via the valve and controlled by the air pump pad 320 and the pressure release valve 330.

FIG. 4. illustrates a front view of the under belt 300 with the inflatable air chamber system, according to one embodiment. In some embodiments, the under belt 300 includes heavy duty nylon material ribbing 410 and 411 connecting the heavy duty hook and loop material 420 (e.g., either hook or loop material to be connected with the opposite connecting material) with a hook and loop buckles 310 and 311 on each end. In some embodiments, the edge of the entire under belt 300 may be constructed with a heavy-duty nylon ribbing material 410 and 411 (or other similar material) for maximum structural integrity and help protect the internal air chambers 340 (FIG. 3).

FIG. 5. illustrates a rear view of a duty belt system inflatable pad 500, according to one embodiment. In some embodiments, the duty belt system inflatable pad 500 is an optional accessory and may be implemented with the duty belt system or not. In some embodiments, the duty belt system inflatable pad 500 includes a heavy duty nylon material structure with a heavy duty (e.g., 1½ inch) hook and loop material strip 540, and heavy duty nylon material belt keepers 515 including hook and loop fasteners 530/531 and a pocket (or compartment) 510 to conceal an air pump valve system (e.g., a manual squeeze or press pump, a valve and compressed air cylinder system, a battery or rechargeable pump system, etc.). It should be noted that the pocket 510 may be a heavy duty zipper, hook and loop fastening closure, snaps, etc. It should also be noted that one embodiment includes three (3) belt keepers 515, and other embodiments may include more or less belt keepers 515 as desired for fitment.

In one or more embodiments, duty belt system inflatable pad 500 may have a width between 4 inches to 7 inches, preferably 5 inches. In some embodiments, the duty belt system inflatable pad 500 may be constructed with a heavy-duty nylon material 520 (or other similar material) on one exterior side and a heavy duty non-slip neoprene material 610 (FIG. 6) or similar material on the other exterior side. In one embodiment, the edge of the entire duty belt system inflatable pad 500 is constructed with a heavy-duty nylon ribbing material (or other similar material) for maximum structural integrity.

In one embodiment, the heavy duty hook and loop material that runs horizontally in direction down the center of the duty belt system inflatable pad 500 with nylon belt keepers 515 (FIG. 5) that are sewn underneath the hook and loop material 540, may be equally spaced out from one another. The belt keepers 515 may include a hook and loop material 530/531 as a fastening buckle, or similar material. In other embodiments, other types of fastening connections may be implemented for the connectors 530/531 (e.g., snapping loops, twist turn connectors, etc.). In one embodiment, the duty belt system inflatable pad 500 may be integrated as part of the under belt 300.

Figure 6:
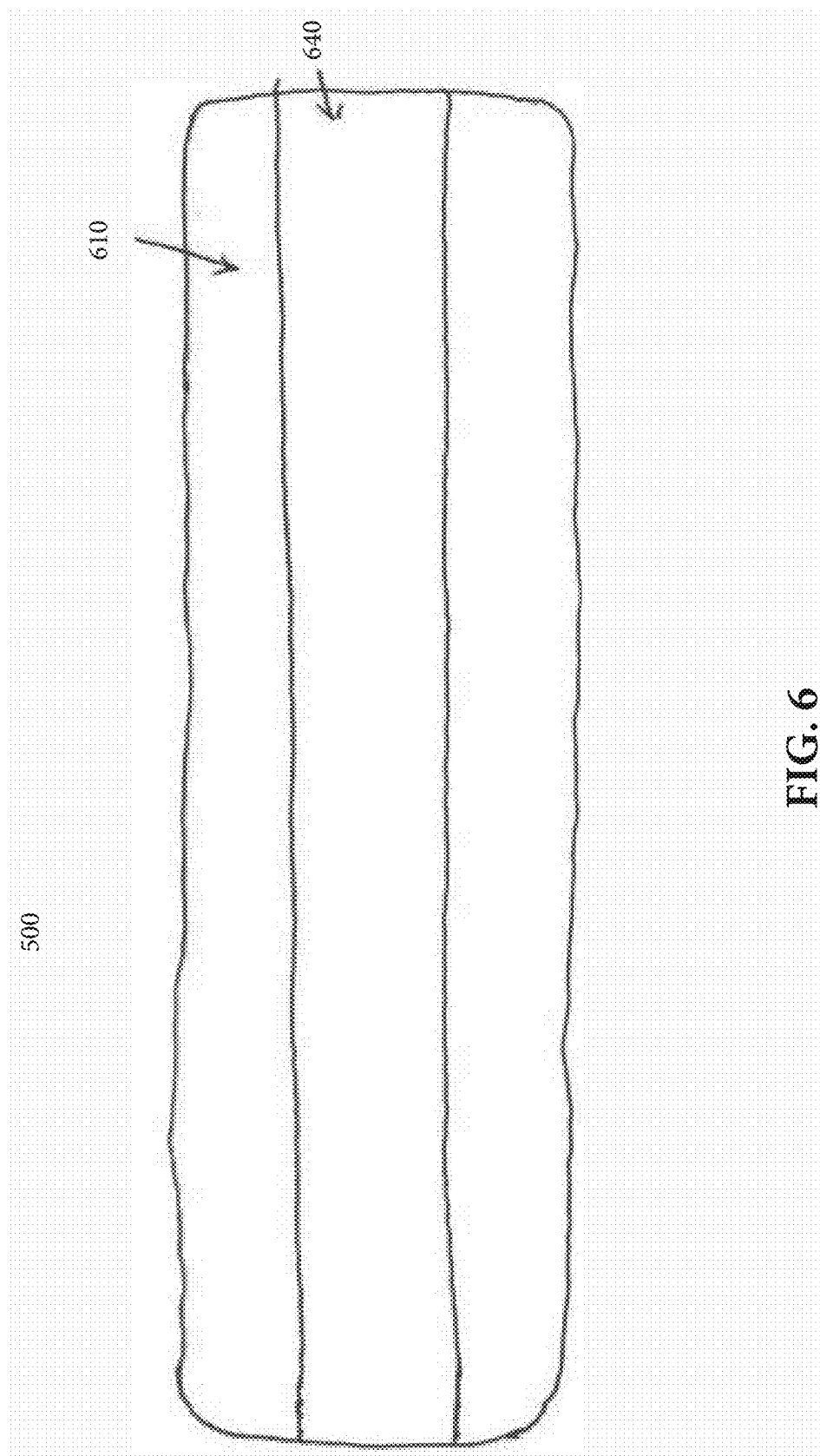
FIG. 6 illustrates a front view of the duty belt system inflatable pad, according to one embodiment.

FIG. 6. illustrates a front view of the duty belt system inflatable pad 500, according to one embodiment. The external front view of the duty belt system inflatable pad 500 shows a heavy duty non-slip neoprene material 610 with a heavy duty (e.g., 1½ inch) hook and loop fastening strip 640 (e.g., either hook or loop material to be connected with the opposite connecting material). The exterior side of the duty belt system inflatable pad 500 made of the neoprene material 520 also has a 1½ inch heavy duty hook and loop material 640 running horizontally in direction down the center of the duty belt system inflatable pad 500. The exterior side of the duty belt system inflatable pad 500 is made of heavy-duty nylon material (or other similar material).

Figure 7:
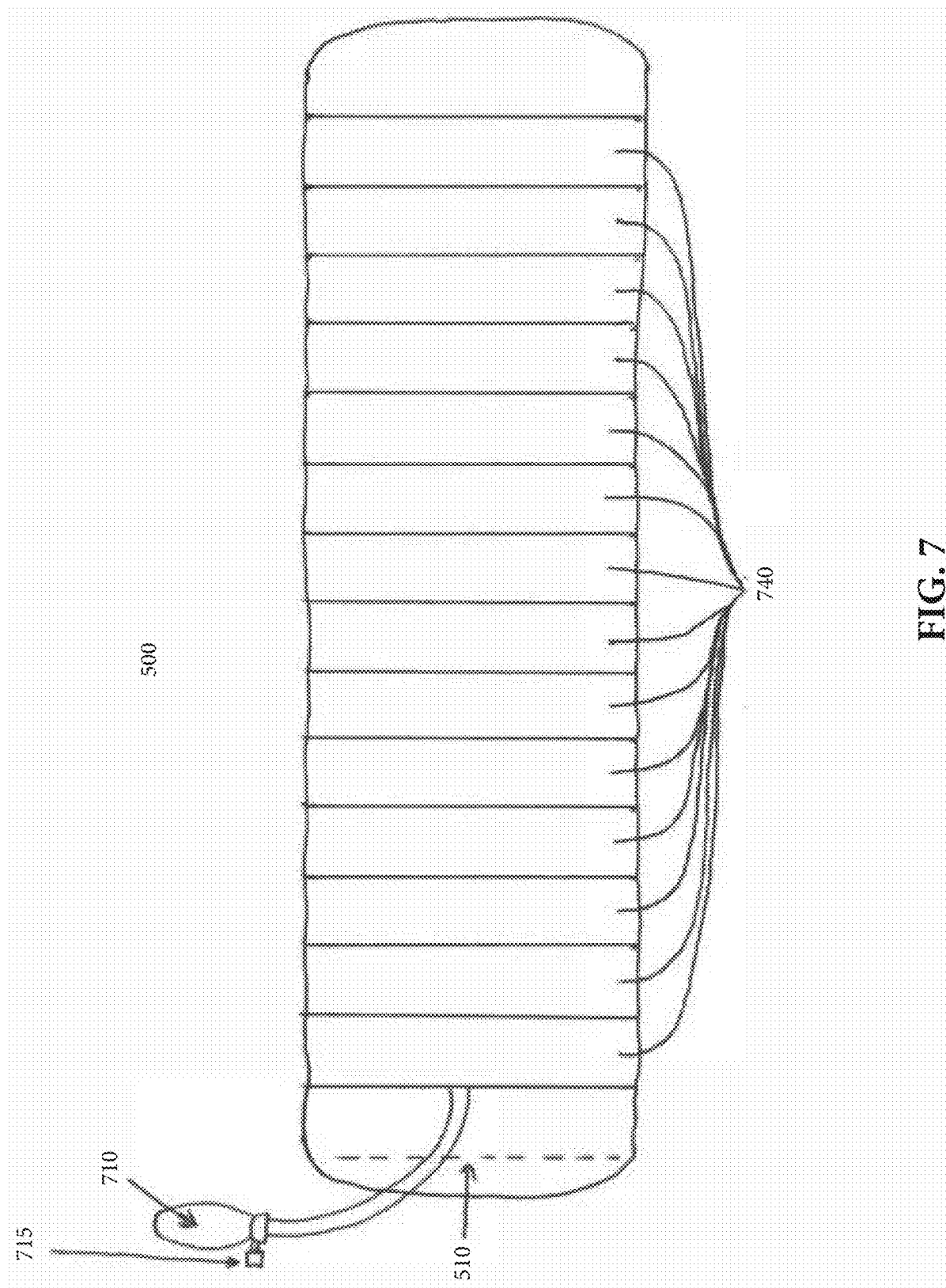
FIG. 7 illustrates an internal view of the duty belt system inflatable pad, according to one embodiment.

FIG. 7. illustrates an internal view of the duty belt system inflatable pad 500, according to one embodiment. In one example embodiment, the internal view of the duty belt system inflatable pad 500 shows the inflatable air chamber system including air chambers 740 and the pocket 510 to conceal the air pump 710 and valve 715 system. It should be noted the air pump 710 and valve 715 system may be replaced with a battery or rechargeable powered pump device or a cylinder-based inflation system. In other embodiments, the pump 710 may be removable or used for inflation of the air chambers 740 through just a valve stem. In one embodiment, the air chambers 740 may be vertical or horizontal, and may be interconnected for receiving air or removal of air, or may each be separately controlled for air inflation/deflation for a customized fitment/deployment. In other embodiments, sections of the air chambers 740 may be connected for air inflation/deflation together. In yet another embodiment, the air chambers 740 may be separated in upper and lower chambers, or organized in multiple sections for customized inflation/deflation.

In some embodiments, the interior of the duty belt system inflatable pad 500 comprises multiple air chambers 740 that may be made with a heavy duty rubber (or other similar material) material, which allows the wearer to adjust the firmness of the duty belt system inflatable pad 500. In one embodiment, the entire edge of the duty belt system inflatable pad 500 is constructed with a heavy duty nylon (or other similar material) ribbing material for maximum structural integrity and help protect the internal air chambers 740.

In some embodiments, the air pump 710 may be an automatic system (e.g., from an electrical pump, a compressed air container, air cylinder system, etc.) and controlled by a chip or microprocessor including at least one processor, memory and power supplied by at least one battery, a USB port, etc., and may be used to set the belt pad to a desired pressure via a gauge, readout, etc. In one embodiment, the automatic air pump may have a memory function to save one or more desired settings (e.g., for a seated use case, for a working, walking, standing, etc. use case, etc.) and a selection button, switch, etc.

FIG. 8. illustrates a rear view of a duty belt 800, according to one embodiment. In one embodiment, the duty belt 800 is made of heavy duty nylon (e.g., 2 inches wide, etc.) and attaches to the inflatable pad 500 (FIGS. 5-7) and includes the heavy duty belt buckle 100 that includes the first portion 105 and the second portion 120, heavy duty elastic material portions 810 and 811 that attach to respective heavy duty tri-glides 200 and the first and second portions 105 and 120 of the heavy duty belt buckle 100. In one embodiment, the elastic material portions 810 and 811 are replaceable.

In some embodiments, the duty belt 800 is the fully adjustable includes a heavy duty nylon material 820 (or other similar material) on the exterior/rear side and a heavy duty hook and loop material 920 (FIG. 9) on the other exterior/front side. Each end of the heavy duty nylon portion 820 of the duty belt 800 loops around a stainless steel (or other similar material) pin 210/211 which are each removable from the heavy duty plastic (or other similar material) tri-glides 200. A piece (e.g., 2 inches by 2¼ inch, etc.) of heavy duty elastic material 810/811 (or other similar material) with sewn loops on each side wraps (loops) around the other stainless steel pin 211/210 on the opposite side of the tri-glides 200. The first portion 105 of the heavy duty belt buckle 100 attaches to the elastic material 811 by removing the stainless steel pin 110 (FIG. 1) from the heavy duty belt buckle 100 and sliding the stainless steel pin 110 back in through the first portion 105 of the heavy duty belt buckle 100 and sewn loop in the elastic material 811. The second portion 120 of the heavy duty belt buckle 100 attaches to the opposite side of the duty belt 800 is a similar way. The majority of the adjustments are made by adjusting the nylon part 820 of the duty belt 800 around the stainless steel pins 210/211. The heavy duty elastic material 810/811 (or other similar material) provides for adjustments to be made by the wearer to accommodate different uniform waist sizes.

FIG. 9. illustrates a front view of the duty belt 800, according to one embodiment. In some embodiments, the front view of the duty belt 800 includes a heavy-duty hook and loop material strip 920 for the length of the whole duty belt 800. In some embodiments, the first step to using the duty belt system is to loop the under belt 300 through the user's pant loops just like with a typical belt, where the hook and loop material 420 side is positioned away from the user's body. The second step is to attach the duty belt system inflatable pad 500 (FIGS. 5-7) to the under belt 300 with the hook and loop material 420 by placing the neoprene material 610 side of the duty belt system inflatable pad 500 towards the user's back and wrapping the duty belt system inflatable pad 500 around the user's waist. The next step is to place the assigned duty equipment on the duty belt 800 and then attach the duty belt 800 to the duty belt system inflatable pad 500 with the hook and loop material 640 (FIG. 6) and securing it with the heavy duty nylon belt keepers 515.

The duty belt 800 may be made in multiple different lengths, such as to fit small, medium, large, etc. sized users. In one embodiment, other forms of gas may be used instead of air, such as nitrogen or carbon dioxide via cartridges or other inflator devices. In some embodiments, instead of gas (e.g., air, carbon dioxide, nitrogen, etc.), gel or a liquid may be inserted into the air chambers, which may be converted from an air chamber to a liquid or gel chamber as needed.

In some embodiments, the duty belt system (including the under belt 300, duty belt 800 and the duty belt system inflatable pad 600) provides adjustable firmness, is light weight, is easy to wear/use with the hook and loop material, eliminates belt pinch, eliminates constant adjusting of the duty belt when wearing a different uniform, reduces the percentage of lower back and sciatica issues and may reduce the number of workers compensation cases.

Figure 10A:
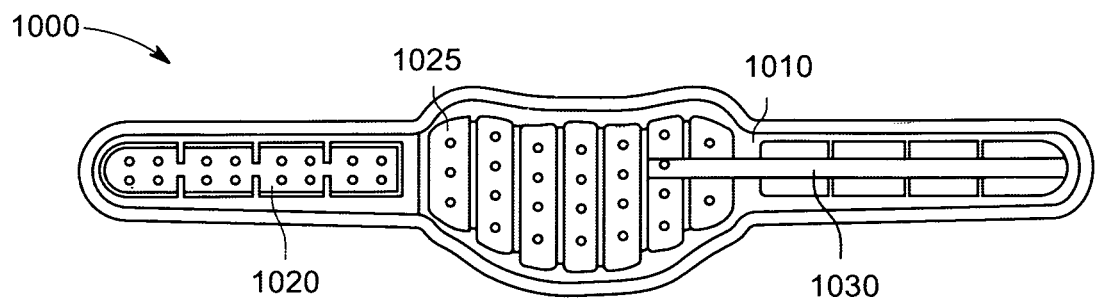
FIG. 10A illustrates an internal/external view of an interior side of a second layer of a duty belt system, according to one embodiment.

FIG. 10A. illustrates an internal/external view of an interior side of a second layer (layer 2 or middle belt) 1000 of a duty belt system, according to one embodiment. In one embodiment, the second layer 1000 includes a breathable or mesh fabric material 1010 over padding (e.g., foam, etc.) formed on air bladders 1020 and 1025. In one embodiment, the air bladders are inflated using the air bladder pumps (e.g., push pumps that fill with air that is pushed using a user's finger or thumb to force the air into the air bladders with a one way valve) and release valves 1040 (FIG. 10C) that release the air form the air bladders. The second layer 1000 of the duty belt system includes a portion of hook and loop fastener portion 1030 that attaches to a first layer (or layer 1) 1130 hook and loop fastener portion 1035 that is worn by a user on clothing (e.g., pants, shorts, etc.).

Figure 10B:
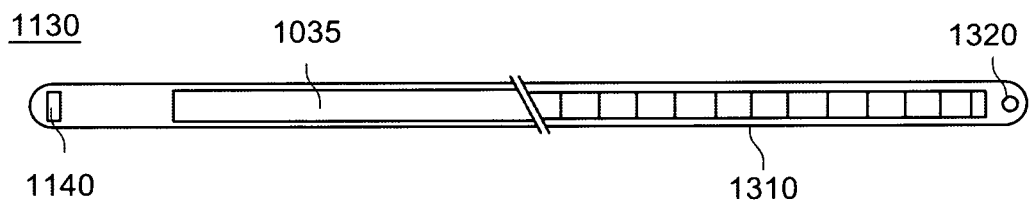
FIG. 10B illustrates an internal/external view of an exterior side of a first layer of a duty belt system, according to one embodiment.

FIG. 10B. illustrates an internal/external view of an exterior side of the first layer 1130 of the duty belt system, according to one embodiment. In one embodiment, the first layer 1130 includes padding (or padding segments), 1310 (e.g., foam, etc.) internally. In one embodiment, a ring pull tab 1320 (e.g., a metal ring, hardened plastic ring, etc.) is included for pulling the first layer 1130 tightly around a user's waist. In one embodiment, a fastening loop 1140 is disposed on one end of the first later 1130. In one embodiment, the first layer 1130 is fastened similarly as with under belt 300 (FIG. 3) using hook and loop fasteners.

Figure 10C:
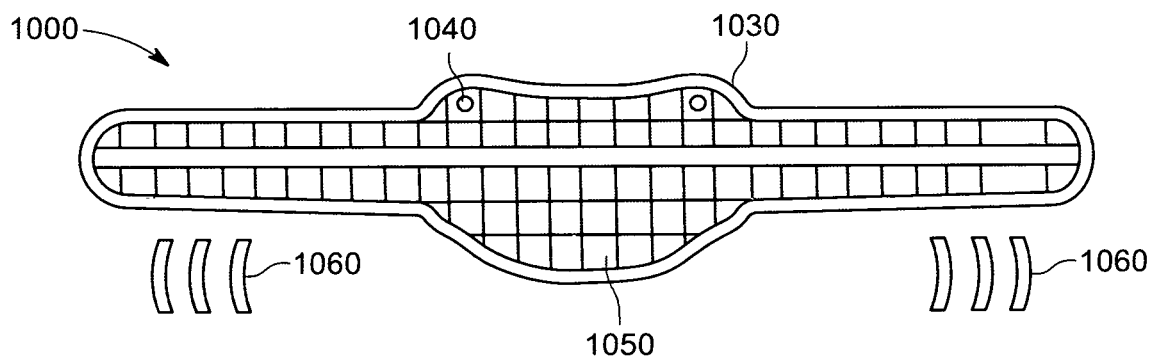
FIG. 10C illustrates an external view of the exterior side of the second layer of a duty belt system, according to one embodiment.

FIG. 10C. illustrates an external view of the exterior side of the second layer 1000 of a duty belt system, according to one embodiment. In one embodiment, the second layer 1000 includes multiple air bladder pumps and release valves 1040. The outer portion of the second layer 1000 may be laser cut modular lightweight load-carrying equipment (MOLLE) type of material, such as a network of nylon webbing attached to a framework and formed at regular intervals creating channels, etc. In one embodiment, attachable belt loops 1060 are removably attached to the second layer 1000 for attachment to a third layer (or layer 3) duty belt 800 (see FIGS. 8 and 9 and 10D).

Figure 10D:
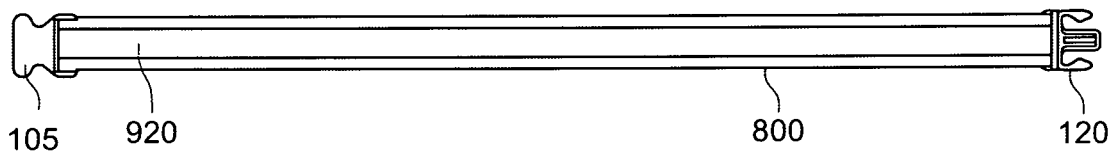
FIG. 10D illustrates an external view of an interior side of a third layer of a duty belt system, according to one embodiment.

FIG. 10D illustrates an external view of an interior side of a third layer duty belt 800 of a duty belt system, according to one embodiment. The duty belt 800 includes the belt buckle 100 (see also, FIG. 1) including the first portion 105 and the second portion 120. The duty belt 800 also includes the heavy duty hook and loop material 920 (see also FIG. 9) for attachment to the hook and loop fastener portion 1030 of the second layer 1000. In one embodiment, the duty belt 800 is adjustable using the elastic material portions 810 and 811 (FIG. 8).

Figure 11:
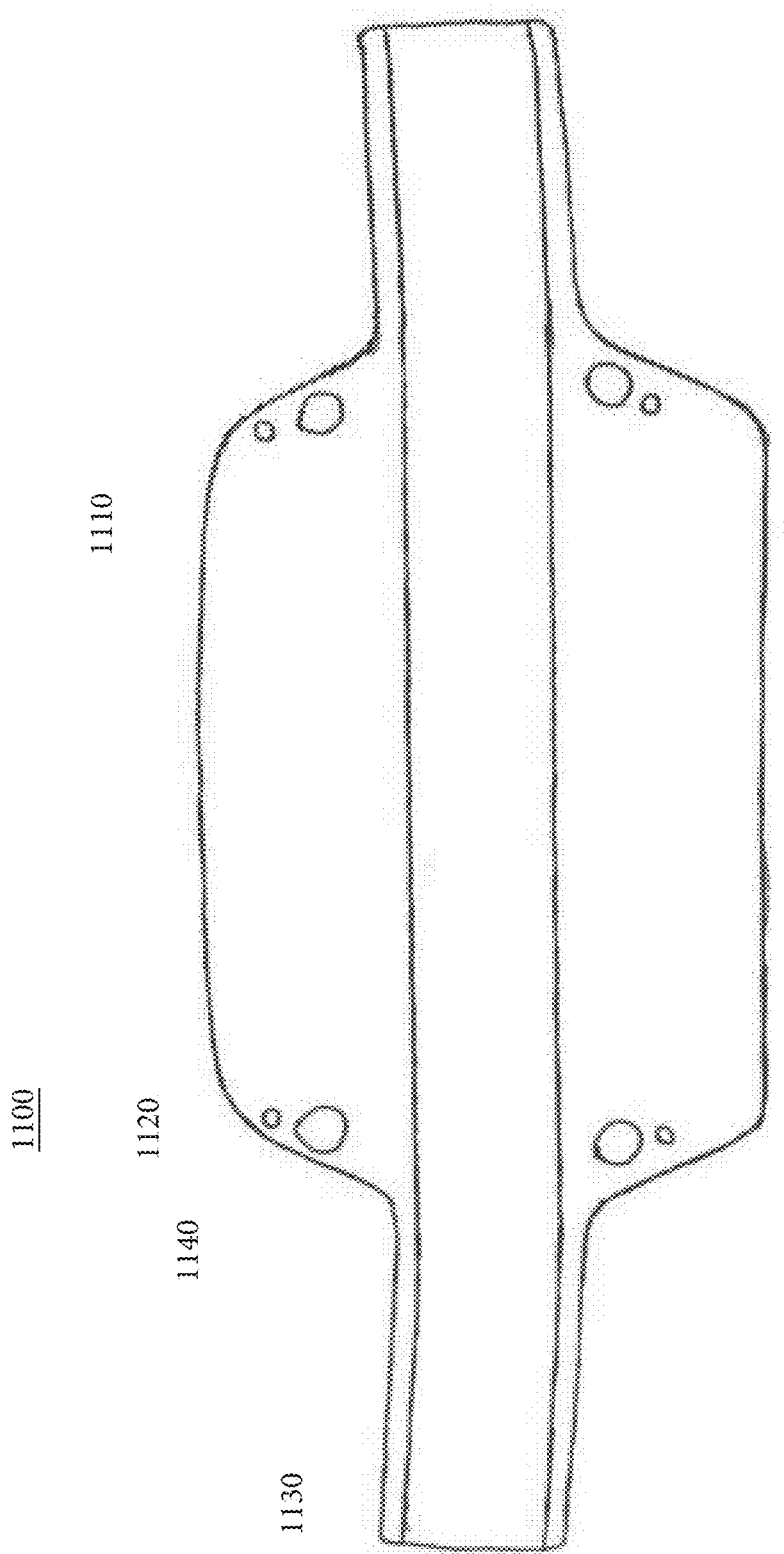
FIG. 11 illustrates an external view of an exterior side of a belt pad of a duty belt system, according to one embodiment.
Figure 17:
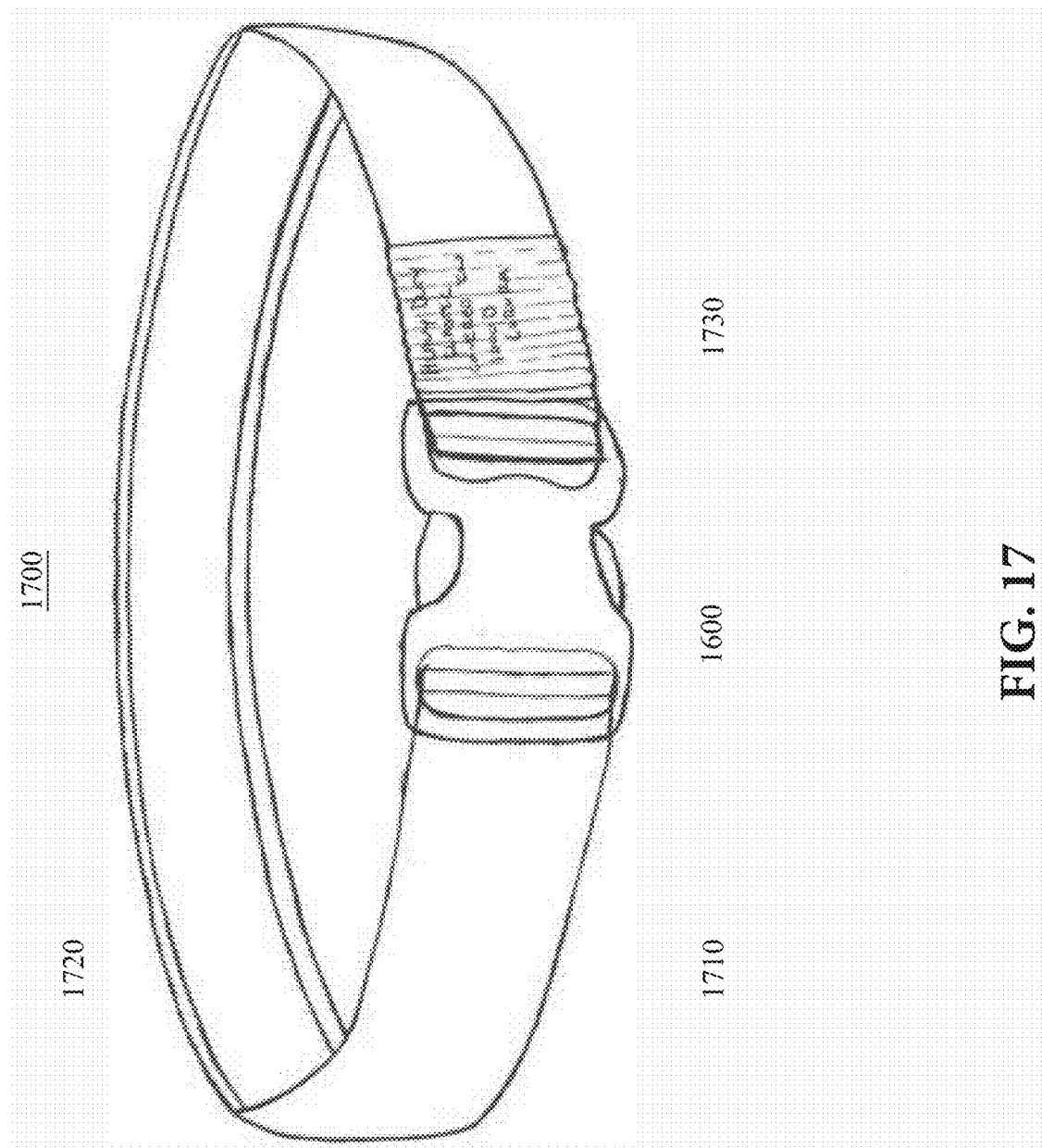
FIG. 17 illustrates a front view of a duty belt of a duty belt system, according to one embodiment.

FIG. 11 illustrates an external view of an exterior side of a belt pad or second layer 1100 of a duty belt system, according to one embodiment. The belt pad 1100 is a second layer (layer 2 or middle belt) of a duty belt system, according to one embodiment. In one embodiment, the second layer 1100 includes CORDURA® material 1110 on the exterior side (e.g., 1000 denier, etc.). In one embodiment, the second layer 1100 includes a pump 1140 (see also FIG. 13 with a release valve 1120, and a hook (of hook and loop fasteners that connect to one another) type fastener portion 1130 (e.g., 2 inches wide, etc.) covering most or all of the second layer exterior side (which attaches via the hook type fastener portion 1130 to a loop type fastener portion 1720 of a duty belt or third layer 1700 (FIG. 17). The pumps 1140 may be separate for each of multiple air bladder portions (e.g., left and right side bladder portions 1160 and back pad bladder systems 1150, FIG. 12). The air bladder systems 1150 and 1160 are inflated using the pumps 1140 and release valves 1120 that release or adjust the air form the air bladder systems 1160 and 1160.

Figure 12:
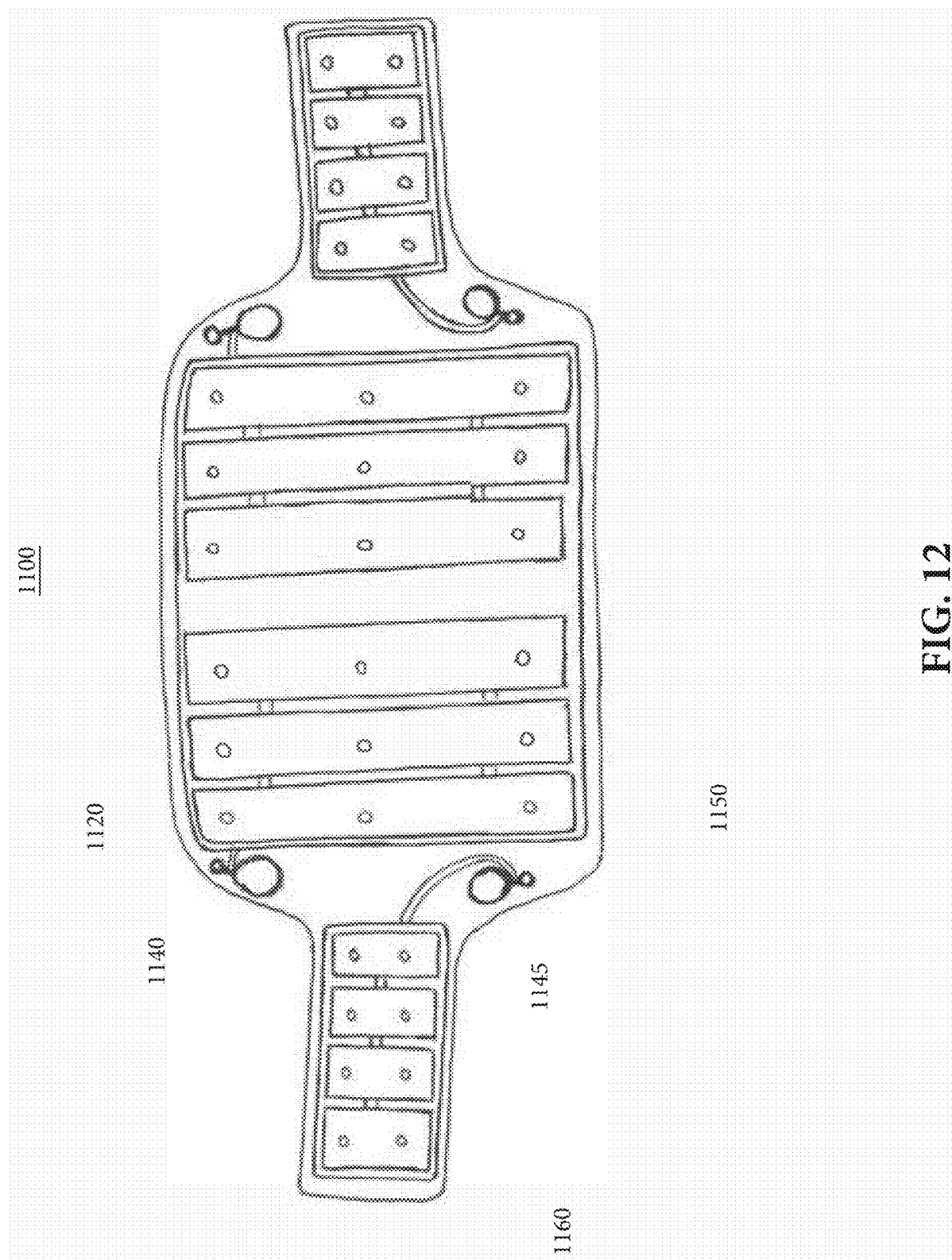
FIG. 12 illustrates an internal view of the belt pad of a duty belt system, according to one embodiment.

FIG. 12 illustrates an internal view of the belt pad or second layer 1100 of a duty belt system, according to one embodiment. In one embodiment, the second layer 1100 includes multiple sets of air bladder portions 1150 and 1160 that are sized and placed within the interior area of the second layer 1100. In one embodiment, shorter air bladder portions 1160 are disposed within the interior portion of the second layer 1100 for the left and right sides of the second layer 1100. In one embodiment, longer air bladder portions 1150 are disposed within the interior portion of the second layer 1100 for the left and right rear or back portions of the second layer 1100. In one embodiment, the sets of air bladder portions 1150/1160 each are controlled by a separate pump 1140 with release or bleed valve 1120 via an air line 1145. In other embodiments, more or less sets of air bladder portions 1150/1160 may be employed depending on the design or requirements, based on size of the second layer 1100, etc.

Figure 13:
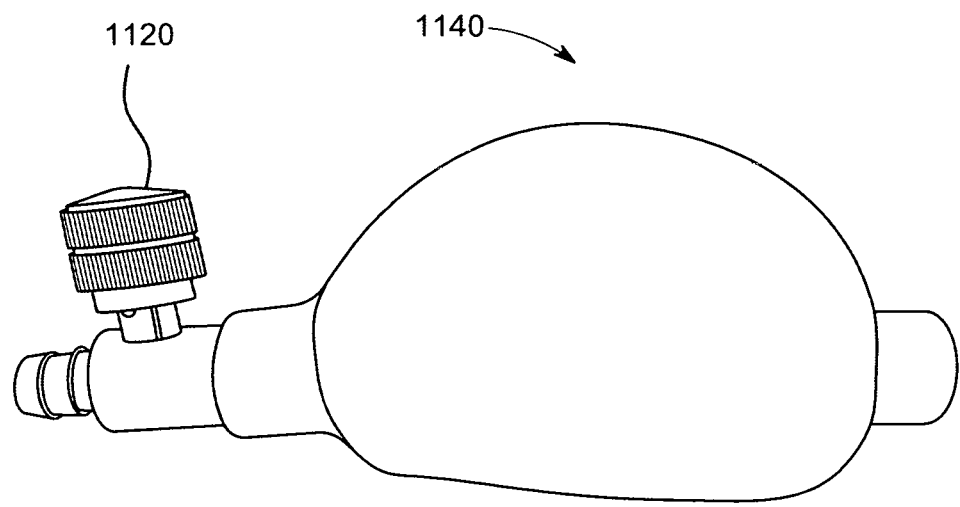
FIG. 13 illustrates a photograph of a manual air pump and bleed valve for a duty belt system, according to one embodiment.

FIG. 13 illustrates a photograph of a manual air pump 1140 and release or bleed valve 1120 for a duty belt system, according to one embodiment.

Figure 14:
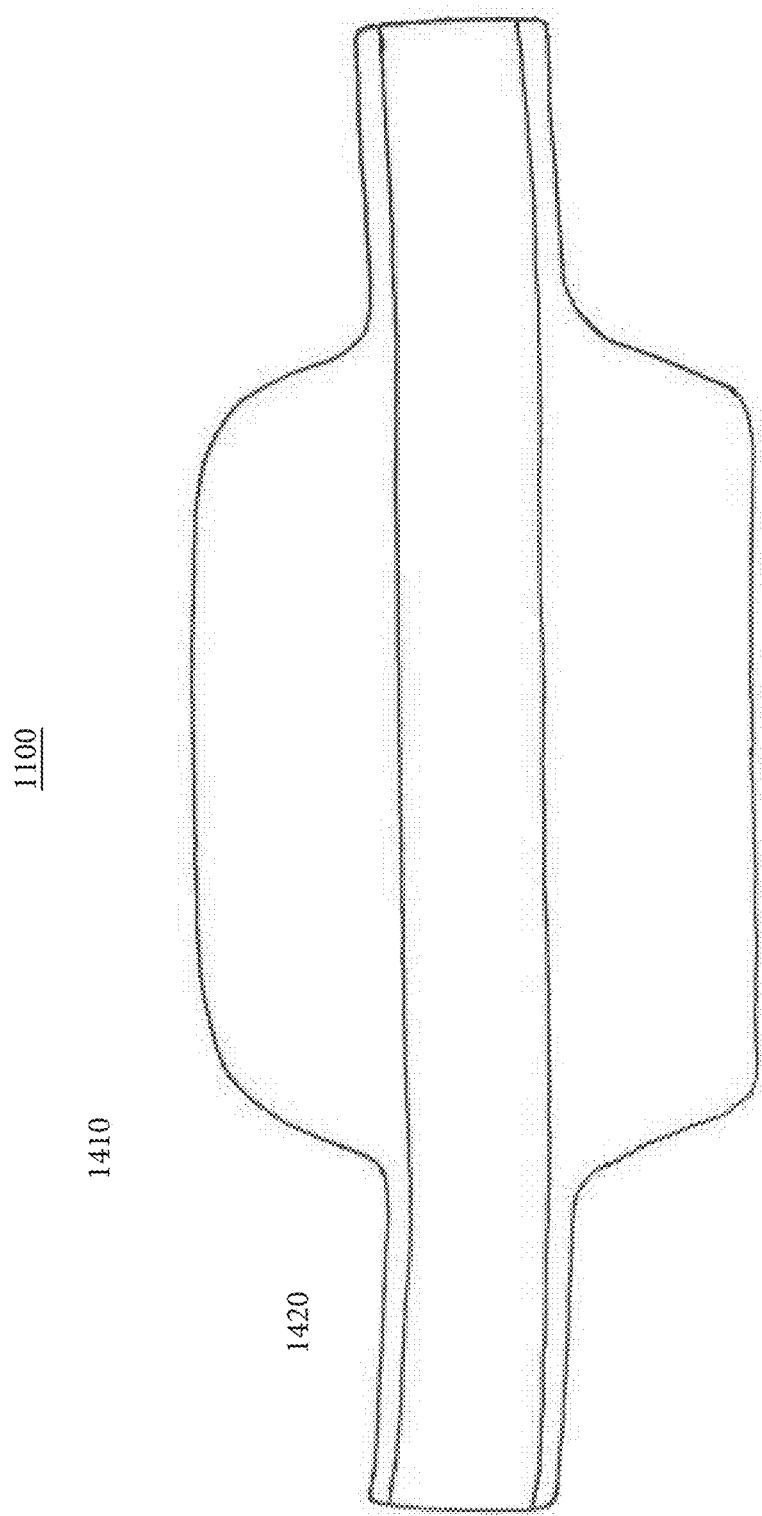
FIG. 14 illustrates an external view of an interior side of a belt pad of a duty belt system, according to one embodiment.

FIG. 14 illustrates an external view of an interior side 1410 of the belt pad or second layer 1100 of a duty belt system, according to one embodiment. The interior side 1410 (the side that faces a user's back) may be covered with an anti-slip material, such as neoprene, etc. A loop portion 1420 of a hook and loop fastener system is attached near the center horizontal portion of the interior side 1410 of the second later 1100. The loop portion 1420 attaches to the hook portion 1520 of the inner belt or first layer 1500 (FIG. 15).

Figure 15:
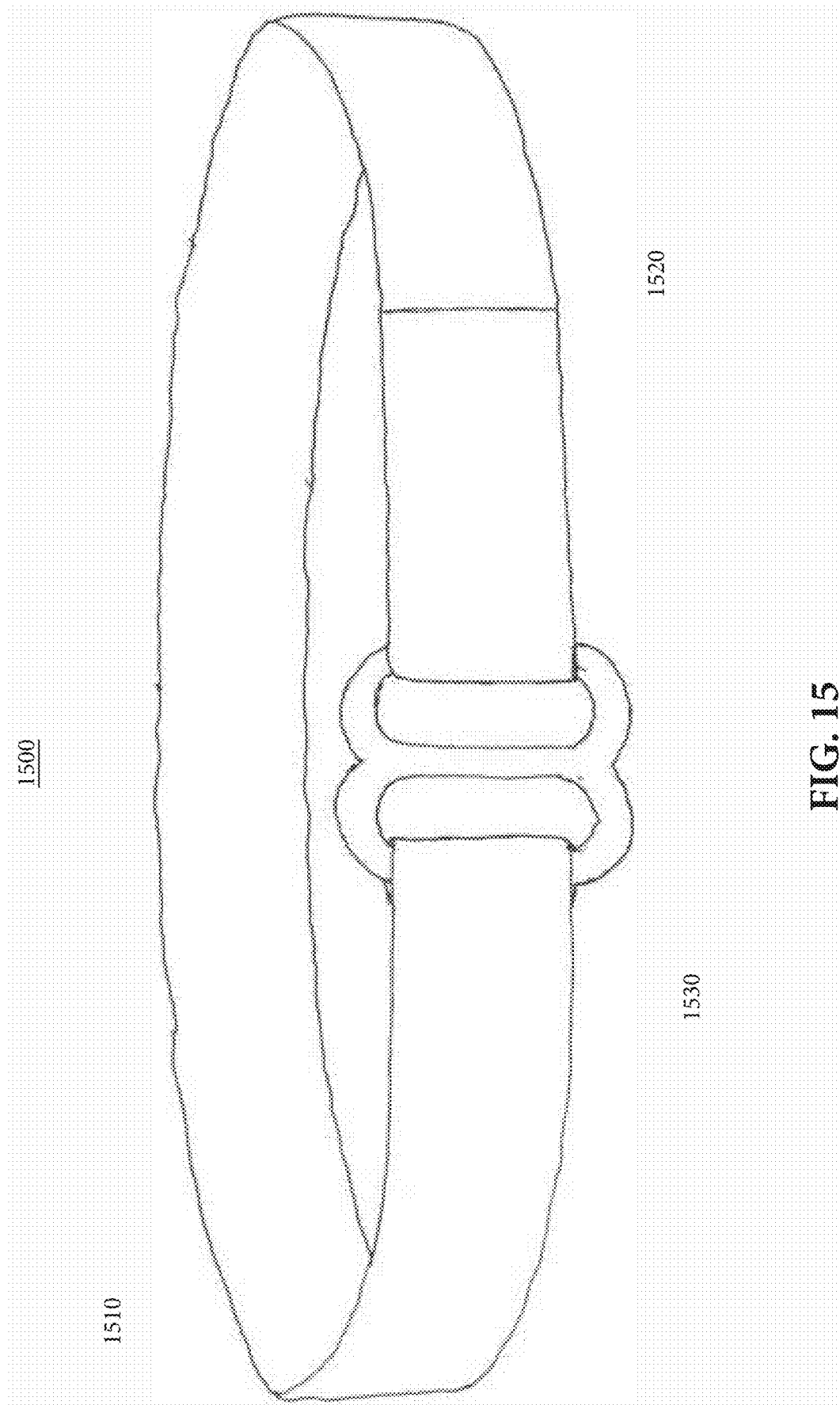
FIG. 15 illustrates a front view of another under belt of a duty belt system, according to one embodiment.

FIG. 15 illustrates a front view of another under belt or first layer 1500 of a duty belt system, according to one embodiment. In one embodiment, the first layer 1500 includes webbing material 1510 (e.g., nylon webbing, two inches wide, etc.), the hook portion 1520 and a buckle or loop connection portion 1530. In one embodiment, the first layer 1500 attaches to a user's pants/trousers/shorts/etc., with the second layer 1100 attaching on the outer perimeter of the first layer 1500.

Figure 16:
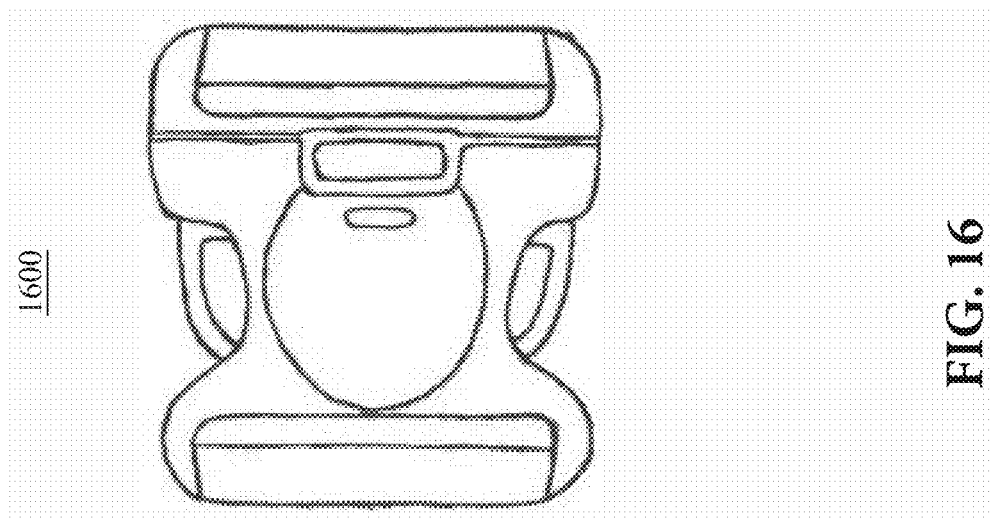
FIG. 16 illustrates a front view of a snap lock buckle for a duty belt of a duty belt system, according to one embodiment.

FIG. 16 illustrates a front view of a snap lock buckle 1600 (e.g., a cop lok heavy duty buckle, etc.) for a duty belt or third layer 1700 (FIG. 17) of a duty belt system, according to one embodiment.

Figure 18:
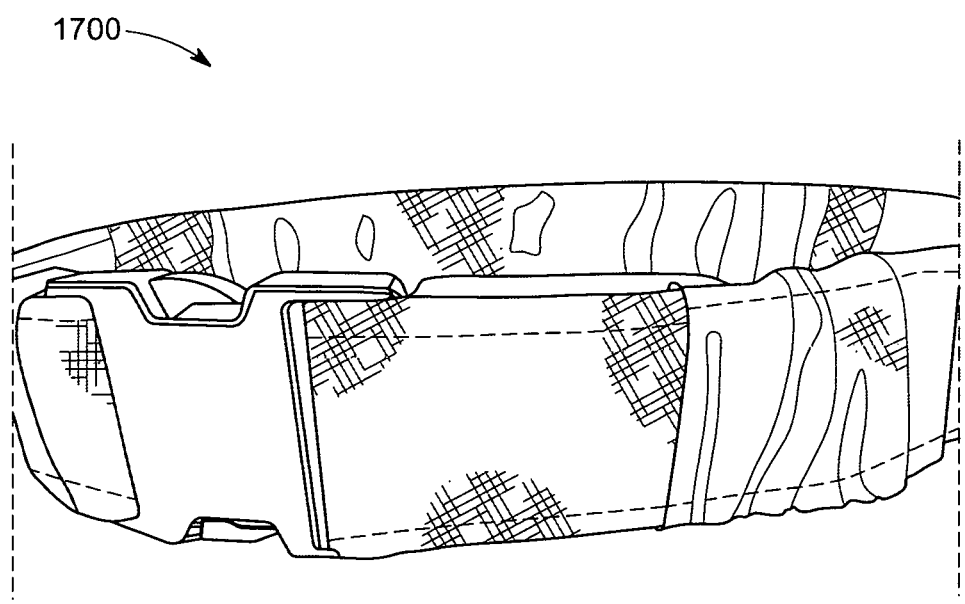
FIG. 18 illustrates a photograph of the duty belt of a duty belt system, according to one embodiment.

FIG. 17 illustrates a front view of a duty belt or third layer 1700 of a duty belt system, according to one embodiment. The third layer 1700 includes the snap lock buckle 1600, webbing portion 1710 (e.g., nylon webbing, nylon webbing sandwiching foam padding, etc.), heavy duty loop portion 1720 and heavy duty elastic material covered in CORDUIRA®. FIG. 18 illustrates a photograph of the duty belt or third layer 1700 of a duty belt system, according to one embodiment. In one embodiment, the third layer 1700 attaches to the second layer 1100 via the loop portion 1720 that fastens/attaches to the hook portion 1130; the loop portion 1420 of the second layer 1100 fastens/attaches to the hook portion 1520 of the first layer 1500.

References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system comprising:
   an under belt that includes:
      a first under belt side including a first hook and loop fastener strip;
      a second under belt side coupled to the first under belt side, the second under belt side including a first heavy duty material outer portion; and
      an inner under belt portion disposed between the first under belt side and the second under belt side, the inner under belt portion including padding material;
   a middle belt including a plurality of expandable padding portions; and
   a duty belt that includes:
      a center duty belt portion having a first duty belt side and a second duty belt side;
      a first elastic end coupled to the center duty belt portion and a first belt buckle portion; and
      a second elastic end coupled to the center duty belt portion and a second belt buckle portion;
   wherein:
      the first duty belt side including a second hook and loop fastener strip;
      the second duty belt side including a second heavy duty material outer portion; and
      the middle belt is removably coupled to the duty belt.

2. The system of claim 1, wherein the middle belt further comprises:
   a first pad side including a third hook and loop fastener; and
   a second pad side including a fourth hook and loop fastener strip and a flexible material;
   wherein the plurality of expandable padding portions are each disposed between the first pad side and the second pad side.

3. The system of claim 2, wherein the plurality of expandable padding portions comprises a plurality of expandable air chambers.

4. The system of claim 3, wherein the expandable air chambers comprise a plurality of air bladder sets.

5. The system of claim 4, wherein each air bladder set of the plurality of air bladder sets is coupled with a pump system.

6. The system of claim 5, wherein:
   a first air bladder set includes air bladders that each have a first size; and
   a second air bladder set includes air bladders that each have a second size.

7. The system of claim 6, wherein the first size is greater than the second size.

8. The system of claim 5, wherein the duty belt center portion includes a first webbing layer, a second webbing layer and a padding layer disposed between the first webbing layer and the second webbing layer.

9. The system of claim 5, wherein:
   the pump system comprises one of:
   a first hand air pump and a first release valve;
   a first battery operated air pump and the release valve; or
   a first cylinder including compressed gas and the release valve.

10. A system comprising:
    an under belt that includes:
       a first under belt side including a first hook and loop fastener strip;
       a second under belt side coupled to the first under belt side, the second under belt side including a first heavy duty material outer portion; and
       an inner under belt portion disposed between the first under belt side and the second under belt side, the inner under belt portion including padding material;
    a duty belt that includes:
       a center duty belt portion having a first duty belt side and a second duty belt side;
       a first elastic end coupled to the center duty belt portion and a first belt buckle portion; and
       a second elastic end coupled to the center duty belt portion and a second belt buckle portion; and
    an expandable padded middle belt removably coupled to the under belt and the duty belt;
    wherein:

the first duty belt side including a second hook and loop fastener strip; and the second duty belt side including a second heavy duty material outer portion.

11. The system of claim 10, wherein the middle belt comprises:
 a first pad side including a third hook and loop fastener;
 a second pad side including a fourth hook and loop fastener strip and a flexible material, the fourth hook and loop fastener strip removably couples to second hook and loop fastener strip; and
 an inner pad portion disposed between the first pad side and the second pad side, the inner pad portion including a plurality of expandable chambers.

12. The system of claim 11, wherein the plurality of expandable chambers comprises a plurality of expandable air bladders.

13. The system of claim 12, wherein the plurality of expandable air bladders comprise a plurality of air bladder sets.

14. The system of claim 13, wherein the middle belt includes a pump system that expands and contracts the plurality of air bladder sets.

15. The system of claim 14, wherein each air bladder set of the plurality of air bladder sets is coupled with a separate air pump of the pump system.

16. The system of claim 14, wherein:
 the pump system comprises one of:
  a first hand air pump and a first release valve;
  a first battery operated air pump and the release valve; or
  a first cylinder including compressed gas and the release valve.

17. A utility belt system comprising:
 an under belt that includes:
  a first under belt side including a first hook and loop fastener strip;
  a second under belt side coupled to the first under belt side, the second under belt side including a first heavy duty material outer portion; and
  an inner under belt portion disposed between the first under belt side and the second under belt side, the inner under belt portion including foam material padding;
 a duty belt that includes:
  a center duty belt portion having a first duty belt side and a second duty belt side;
  a first elastic portion coupled to the center duty belt portion and a first belt buckle portion; and
  a second elastic portion coupled to the center duty belt portion and a second belt buckle portion; and
 an expandable middle belt removably coupled to the under belt and the duty belt, the expandable middle belt including:
  a first pad side including a third hook and loop fastener strip;
  a second pad side including a fourth hook and loop fastener strip, the fourth hook and loop fastener strip removably couples to second hook and loop fastener strip;
  an inner pad portion disposed between the first pad side and the second pad side, the inner pad portion including a plurality of expandable chambers; and
  a pump system that expands and contracts the plurality of expandable chambers;
 wherein:
  the first duty belt side including a second hook and loop fastener strip;
  the second duty belt side including a second heavy duty material outer portion;
  the under belt is removably coupled to the middle belt; and
  the plurality of expandable chambers comprise a plurality of air bladder sets.

18. The utility belt system of claim 17, wherein each air bladder set of the plurality of air bladder sets is coupled with a separate pump system.

19. The utility belt system of claim 17, wherein:
 a first air bladder set includes air bladders that each have a first size;
 a second air bladder set includes air bladders that each have a second size; and
 the first size is greater than the second size.

20. The utility belt system of claim 17, wherein:
 the pump system comprises one of:
  a first hand air pump and a first release valve;
  a first battery operated air pump and the release valve; or
  a first cylinder including compressed gas and the release valve.

* * * * *